United States Patent
Brilman

(10) Patent No.: US 6,975,230 B1
(45) Date of Patent: Dec. 13, 2005

(54) METHOD AND APPARATUS FOR REGISTERING MOVEMENT PATTERNS OF HUMAN BEINGS

(76) Inventor: Arend Jan Brilman, Schout Bij Nacht Doormanlaan 40, Wassenaar (NL) 2243 AM ( * ) Notice: Subject to any disclaimer, the term of this patent is extended or adjusted under 35 U.S.C. 154(b) by 0 days.

(21) Appl. No.: 10/048,204

(22) PCT Filed: Jul. 29, 1999

(86) PCT No.: PCT/NL99/00489

§ 371 (c)(1),
(2), (4) Date: Jun. 3, 2002

(87) PCT Pub. No.: WO01/08556

PCT Pub. Date: Feb. 8, 2001

(51) Int. Cl.[7] .............................................. G08B 23/00

(52) U.S. Cl. ............................. 340/573.1; 340/573.7; 340/575; 340/572.8; 128/721; 128/782

(58) Field of Search ..................... 340/573.1, 573.7, 340/575, 572.8, 539.1, 539.19; 128/721, 128/722, 723, 774, 775, 782; 600/534, 595, 600/484, 529, 536, 323, 449, 481, 483, 300

(56) References Cited

U.S. PATENT DOCUMENTS

| 5,295,490 A | * | 3/1994 | Dodakian ................... 600/534 |
| 5,479,932 A | * | 1/1996 | Higgins et al. ............. 600/529 |
| 5,749,365 A | * | 5/1998 | Magill ........................ 600/484 |
| 5,774,055 A | * | 6/1998 | Pomerantz ............... 340/573.7 |
| 6,011,477 A | * | 1/2000 | Teodorescu et al. ..... 340/573.1 |

FOREIGN PATENT DOCUMENTS

| DE | 4227483 C | 11/1993 |
| EP | 849715 A | 6/1998 |
| WO | WO 9834577 A | 8/1998 |
| WO | WO 9904691 A | 2/1999 |

* cited by examiner

Primary Examiner—Hung Nguyen
(74) Attorney, Agent, or Firm—Hoffmann & Baron, LLP

(57) ABSTRACT

An apparatus for registering a movement pattern of at least one part of the body of an individual, on the basis of a number of parameters, and generating a signal on the basis of at least one pre-set threshold value of at least one parameter or a set movement pattern, comprises at least one sensor part (1) having at least one movement sensor (8), which sensor part is equipped with means (6) for attachment to or onto the individual in question, the at least one part of the body, and a receiver, in particular a base station (20). The apparatus further comprises transmitting means (9) and receiving means (25) for wireless communication between the sensor part (1) and the base station (20), for transfer of at least said signal.

13 Claims, 5 Drawing Sheets

METHOD AND APPARATUS FOR REGISTERING MOVEMENT PATTERNS OF HUMAN BEINGS

This application is the U.S. National Phase of International Application Number PCT/NL99/00489, filed Jul. 29, 1999, which is incorporated herein by reference.

BACKGROUND OF THE INVENTION

This invention relates to a method for registering movement patterns of human beings.

In the care of human beings, in particular relatively young children, such as babies, and patients, for instance, in a hospital, it is of great importance that it can be determined if the individual in question has a correct posture and movement pattern during a particular period of care, so as to prevent, for instance, suffocation or decubitus ulcers. For this purpose, it is conventional to perform visual checks, for instance by walking past the crib or bed, or through video monitoring. This is particularly costly and labor-intensive and moreover may have as a consequence that the individual in question is disturbed while resting. It further requires a physical presence of the attending person and entails a relatively high physical and mental pressure on that person.

In patient monitoring, for monitoring vital body functions such as heart rate and respiration, use is further made of monitoring systems connected directly to the patient, such as respiration equipment or ECG devices. This has as an important disadvantage that such devices entail a great physical and mental pressure on the patient, while moreover such devices are to be connected via cables and tubes, which may entail risks for individuals.

The above-described methods for monitoring an individual further have as an important disadvantage that in each case only the instantaneous situation of the individual in question is checked. This means that decisions will be made merely on the basis of instantaneous data. This increases the risk of wrong decisions, while further there is a risk that between the checks, dangerous, at any rate undesirable, situations arise, which, for instance, have not been anticipated.

From WO 99 04691 A an apparatus and a method is known for monitoring the respiration and movements of an infant to prevent for instance sudden infant death syndrome. To that end the lying position of the infant, that is face down or face up, is detected and compared to a pre-stored threshold value. An alarm may be generated when the threshold value is exceeded. The position is detected by means of a sensor which consists of two parts, a RF generator which is attached to the back of the infant, for instance to its clothing, and a receiving means, which must be mounted in the vicinity of the infant, for instance above its bed. Thus when the infant is lying at his back the signal received by the receiving means will be weaker than when the infant is lying face down.

The object of the invention is to provide a method of the kind described in the introductory part, in which the above-mentioned disadvantages are obviated, while the advantages are maintained. To that end, a method according to the invention is characterized by the features according to claim 1.

SUMMARY OF THE INVENTION

In a method according to the invention, a sensor part is attached to a part of the body of the individual. This sensor part comprises at least one movement sensor with which movements of the part of the body in question, and optionally of the entire individual, can be registered. With the aid of transmitting means included in the sensor part, the information derived from the at least one movement sensor can be wirelessly transferred to a receiver. The movement information is recorded over time and is used as a basis for determining the safety and health situation of the individual in question.

By making use of wireless information transfer, the individual is not hampered, or is hampered to a very minor extent only, by the sensor part, while complete freedom of movement is afforded. Recording the movement history here provides the advantage that on the basis of pattern recognition and/or changes in the pattern in question or, conversely, the absence of such changes, it can be determined whether the individual in question is disposed in a desired position.

In particular in the case or relatively young children, for instance between 0 and 48 months of age, it is of particular importance that the so-called belly position can be registered, since the belly position is generally regarded as an important cause of death for such relatively young children. In a general sense, this is considered to fall within the term of Sudden Infant Death Syndrome or crib death. Without being bound by any theory or limitation, crib death is hereby described as a cause of death in infants and babies, for which (also, in most cases, after autopsy) no directly identifiable medical cause can be established. It basically involves unexpected death of such a young child in crib, bed or the like.

Two important risk factors that can lead to crib death are belly position and side position. Belly position is herein to be understood as at least comprising a position of the child lying on its belly, such that the face at the same time presses into, for instance, the pillow or mattress. Side position is herein to be understood to comprise at least a position in which the child lies on its side, such that an increased risk exists that the child's face is pressed into, for instance, a pillow, mattress or blanket. It will be clear that a risk factor thereby determined for the child is that suffocation occurs or breathing is rendered more difficult, so that death may occur.

Utilizing a method according to the present invention in such young children provides the advantage that the sensor part can be simply attached to the child, for instance to clothing, diaper, wrist or the like, while the receiver can be arranged remotely from the child, for instance adjacent a care giver. On the basis of posture and movement, viewed over time, a signal can then be continuously, periodically or incidentally transmitted to the receiver by the sensor part, depending, for instance, on any deviations from a desired pattern, such that the care givers can be informed remotely from the child. As a consequence, the physical and mental pressure on the care givers is reduced and during a check the child's rest is not disturbed. As a receiver, for instance a specific base station can be utilized, but, for instance, a baby alarm or a telephone may also be used.

In a comparable manner, a method according to the invention can be utilized, for instance, in patients in a hospital, in particular in so-called intensive care units. An additional advantage achieved with a method according to the invention is that the movement history of the individual is recorded, which, if desired, may subsequently be made available for investigation.

A further advantage of a method according to the present invention is that a relatively large number of individuals can be monitored by a limited number of care givers, more specifically by just one care giver.

In an advantageous embodiment, a method according to the invention is characterized by the features according to claim 3.

Using predetermined and set movement patterns, threshold values and the like, the advantage is achieved that simple comparisons between existing and desired conditions can be made and on the basis thereof alert signals can be produced.

The invention further relates to an apparatus for registering a movement pattern of at least one part of the body of an individual, characterized by the features according to claim 5.

With such an apparatus, a method according to the invention can be practiced in a particularly advantageous manner.

In a first advantageous embodiment, an apparatus according to the invention is characterized by the features according to claim 6.

In this embodiment, in a simple and suitable manner, use can be made of a known baby alarm set, for instance a baby alarm set operating off the mains, or a baby alarm set operating on the basis of radio signals. A signal produced by the sensor part can be received by the first baby alarm of the baby alarm set, arranged adjacent the sensor part, and be transmitted to at least a second baby alarm of the same baby alarm set in another room. Such an embodiment of an apparatus according to the invention is relatively inexpensive and simple in use.

In a further elaboration, an apparatus according to the invention is characterized by the features according to claim 7.

The use of an algorithm for comparing the registered movement pattern with predetermined allowable and/or non-allowable movement patterns provides the advantage that a comparison between them is possible in a particular simple and uniform manner. Thus, in a particularly accurate manner, the signaling of situations which may or may not be deviant can occur.

In further elaboration, an apparatus according to the invention is characterized by the features according to claim 8.

The use of memory means provides the advantage that the registered movement history of the individual in question can be stored for a particular time, such that it can be used, for instance, for investigation or prediction.

In a preferred embodiment, an apparatus according to the invention is characterized by the features according to claim 11.

The use of clamping means provides the advantage that the sensor part can be secured relatively easily to, for instance, the individual's clothing, while a smooth relatively flat housing provides the advantage that damage to the individual and the environment is simply prevented, while the individual is not hampered by the housing. Moreover, as a consequence, the chances that the sensor part is unintentionally displaced from its fitted position are considerably reduced. Further, the clamping means have the advantage that the sensor part can be easily stored, for instance by clamping it onto the rim of the crib or bed.

In a still further elaboration, an apparatus according to the invention is characterized by the features according to claim 12.

The use of means for picking up audio signals, such as for instance breathing, heartbeat and the like, provides the advantage that a further monitoring by the care givers is possible, independently of, or in conjunction with, the movement history. In such an embodiment, the apparatus can further function as baby alarm or intercom.

The invention further relates to the use of a movement sensor and transmitting and receiving means for preventing suffocation of human beings, in particular relatively young children, characterized by the features according to claim 14.

Further embodiments of a method and apparatus according to the invention are set forth in the subclaims.

BRIEF DESCRIPTION OF THE DRAWINGS

To clarify the invention, a number of exemplary embodiments of a method and apparatus according to the invention will be described with reference to the drawings, wherein.

DETAILED DESCRIPTION OF THE PREFERRED EMBODIMENTS

Figure 1:
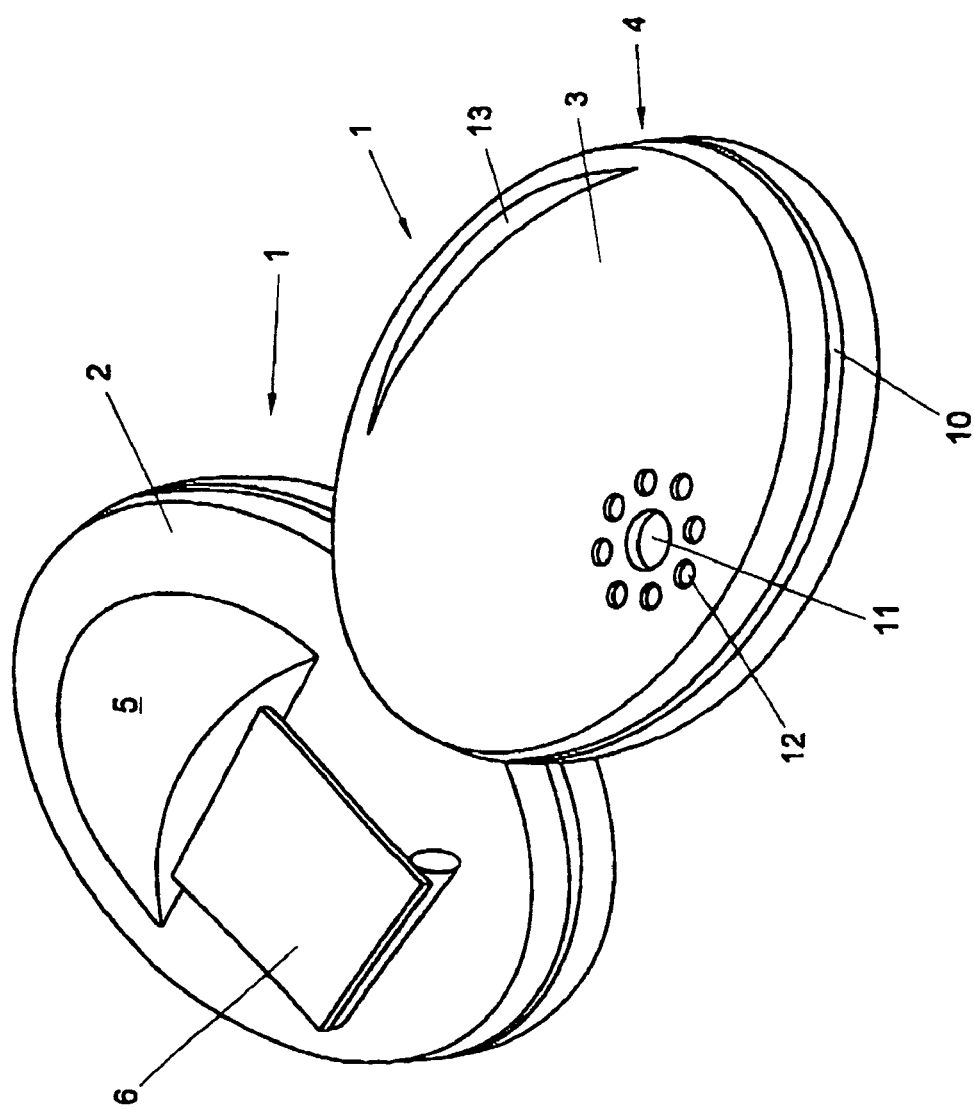
FIG. 1 shows two sensor parts for use in an apparatus according to the invention.

In the drawings, comparable parts have comparable reference numerals.

FIG. 1 shows two sensor parts for use in an apparatus according to the invention, the left-hand side showing the back 2 of a sensor part 1, while the right-hand side shows the front 3 of the second sensor part 1. Each sensor part 1 comprises a housing 4, preferably made, for instance by injection molding, from plastic, which is rounded off on all sides and is relatively small and flat. Fitted on the back 2, with the aid of an elevation 5, is a clip 6, by which the sensor part 1 can be secured to, for instance, a diaper, a shirt, a romper, an infant's sleeping bag or like article of clothing of a child, or to an article of clothing of an adult. Thus, the sensor part can be secured so as to be fixed in position with respect to the individual.

Figure 3:
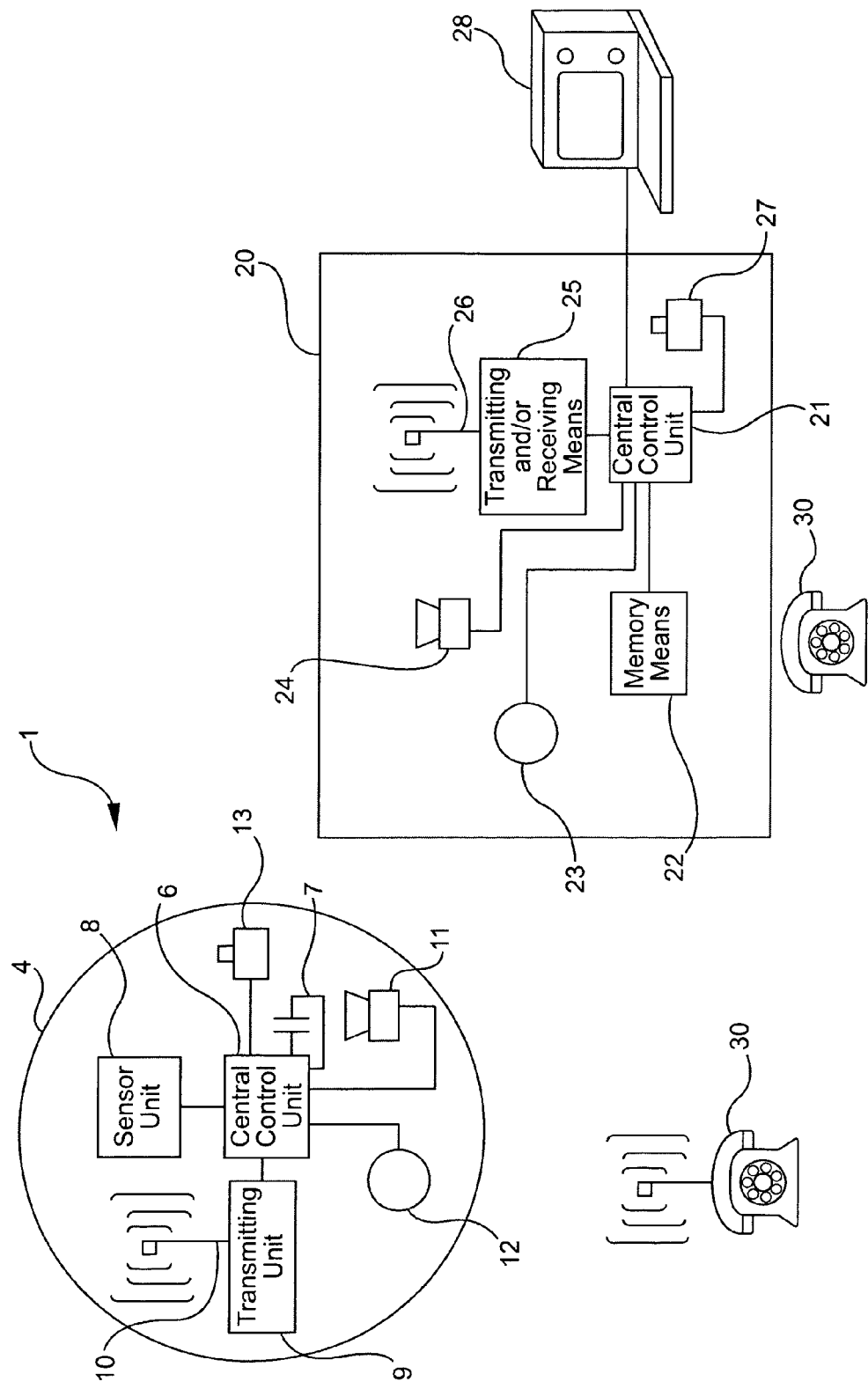
FIG. 3 schematically shows an apparatus according to the invention.

FIG. 3 diagrammatically shows an embodiment of a sensor part 1 according to the invention, in which the housing 4 accommodates a number of electrical and mechanical components, which will be described hereinafter.

The sensor part 1 comprises a central control unit 6, for instance a microchip, supplied by a supply 7, for instance a coin cell or like battery. A sensor unit 8, arranged for registering position and movement of the sensor part 1 is connected with the central control unit 6. The sensor unit 8 will be further elucidated hereinafter.

Further connected to the central control unit 6 is a transmitting unit 9, which, if desired, may further function as receiver, equipped with an antenna 10. Further connected to the central control unit are audio means 11 and visual means 12. The audio means can comprise, for instance, a bleeper or a loudspeaker or like means, as well as, if desired, a microphone. The visual means 12 can comprise, for instance, one or more LEDs or an LCD screen or like display means. An operating means 13 is provided for, for instance, switching the apparatus, in particular the sensor part 1, on and off, resetting same, and the like, as well as inputting and setting parameters, sensitivities and the like.

Figure 2:
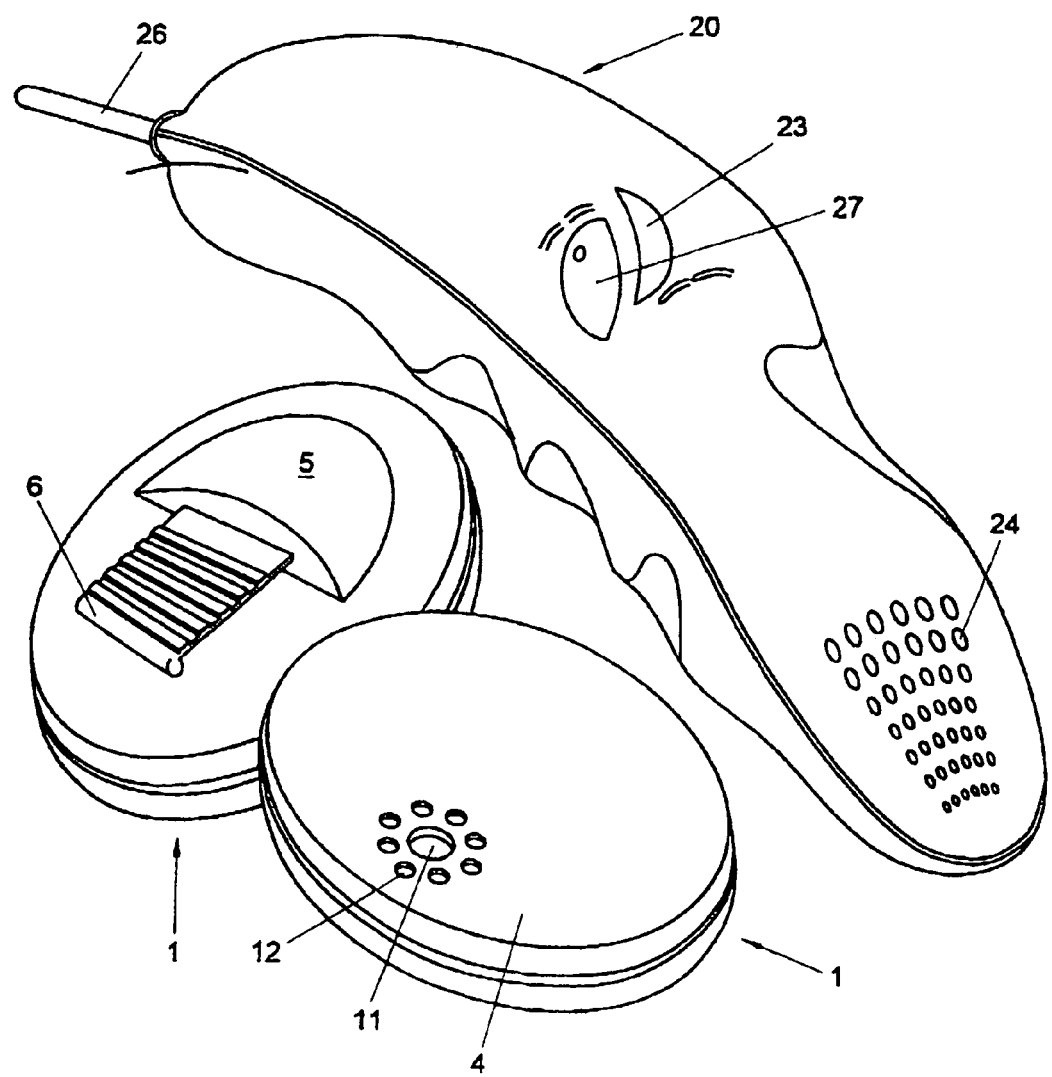
FIG. 2 shows two sensor parts according to the invention together with a base station.

FIG. 2 shows the two sensor parts 1 according to FIG. 1, in a slightly modified embodiment, together with a base station 20, which functions as receiver. In FIG. 3, an embodiment of a base station 20 is represented, which has various components included therein.

The base station 20 comprises a central control unit 21, which is connected with memory means 22 for storing data which have been received from the sensor part 1 and optionally have been processed by the central control unit 21. In addition, again visual 23 and auditory means 24 are connected with the central control unit 21, for producing audiovisual signals on the basis of the processed data. This is to be further discussed hereinafter. The central control unit 21 further comprises transmitting and/or receiving means 25, connected to an antenna 26 for receiving signals emitted by the transmission unit 9 of the sensor part 1 and/or transmitting signals to the sensor part 1. Further, operating means 27 are provided, for instance for switching the receiver 20 on and off, resetting same, and optionally inputting data, as with operating means 13.

An apparatus according to the invention can be used as follows.

Into the central control unit 21 of the receiver 20, for instance by software with the aid of a computer 28 or by hardware, an algorithm is inputted in a suitable manner, for picking up, processing and delivering signals, on the one hand from and to the transmitting and receiving device 25 and, on the other hand, from and to the memory means 22 and the audiovisual means 23, 24. Further, in the central control unit, allowable and/or unallowable movement patterns can be recorded, depending on the application of the apparatus, which can preferably be set and adjusted by the users.

The sensor part 1 is secured with the aid of the clamping means 6 to, for instance, the diaper of a baby (not shown), after which the sensor unit is switched on and reset using the operating means 13. Further, the receiver unit 20 is switched on. During the use of the apparatus, movements of the child in question and/or the absence thereof are registered by the sensor unit 8 and transmitted to the central control unit 6, which processes these signals and leads them further, on the one hand to the audio means 11 and/or the visual means 12 and, on the other hand, to the transmitting means 9, so that the information picked up by the sensor unit 8 is wirelessly transferred to the receiver 20, where the information is processed further in the central control unit 21. This further processing comprises, for instance, a comparison with the priorly inputted allowable and/or unallowable movement patterns. On the basis of this comparison, it is determined by the central control unit whether the baby is safe or that it is plausible that the care giver should intervene. Thus, the sensor unit can determine, for instance, positions such as supine position, belly position and side position, as well as the baby's motional activity. This additionally provides the advantage that the care giver can remotely monitor excessive movement of the child when it makes no sound, for instance when it has cramps or the like. Optionally, a signal can be transmitted from the receiver 20 back to the sensor part 1 for generating a visual or audio signal there, to alert the child. For this purpose, also movement means, for instance a vibrator, could be used.

It will be clear that processing the signals, as well as storing the movement history, can occur both in the sensor part and in the receiver. Recording the movement history has as an advantage that the condition of the individual, in particular the child, can be observed over a long time, so that a better prediction can be made about the position and condition of the child without the child needing to be approached for that purpose, while, further, changes in the condition may possibly be anticipated. Transfer of signals can occur continuously, semicontinuously, periodically or incidentally. In the same way, the information can be reproduced via the visual and/or auditory means on the receiver 20.

As appears from FIG. 3, the receiver 20 can be connected to, for instance, a telephone line, so that the receiver 20 and the sensor part 1 can be remotely operated, for instance switched on and off, reset and listened to, so that contact with the child can be maintained continuously. In a comparable manner, the sensor part 1, in particular the transmitting and receiving unit 9, can be equipped with means for communication with a telephone or like communication means, thus enabling direct communication with the sensor part 1 and optionally with the child. Such embodiments provide the advantage that with the aid of the telephone remote from the receiver and the sensor part 1 contact can yet be maintained.

In an alternative embodiment, the receiver 20 is designed as, for instance, a clip or semaphone-like device, which a care giver can carry with him for maintaining contact with the child.

In a further alternative embodiment, the audio means 11 are arranged for use as both loudspeaker and microphone. This provides the advantage that in addition to the movement registration, audio signals can be recorded as well, for instance the child's breathing, its heartbeat, its crying and talking. In this way, a still better monitoring of the child can be obtained. Moreover, this enables communication with the child even better.

It will be clear that references in the foregoing to babies and children may be understood to include human beings in other age groups, for instance patients in a hospital, in particular in an intensive care unit, where continuous monitoring is desirable or necessary.

Depending on the age and the character of the individual in whom the apparatus is used, the sensitivity of the apparatus, as well as the inputted allowable and/or unallowable movement patterns can be adjusted, since in different categories of people different movement patterns and postures will be allowable, or not, for different periods of time.

Figure 4:
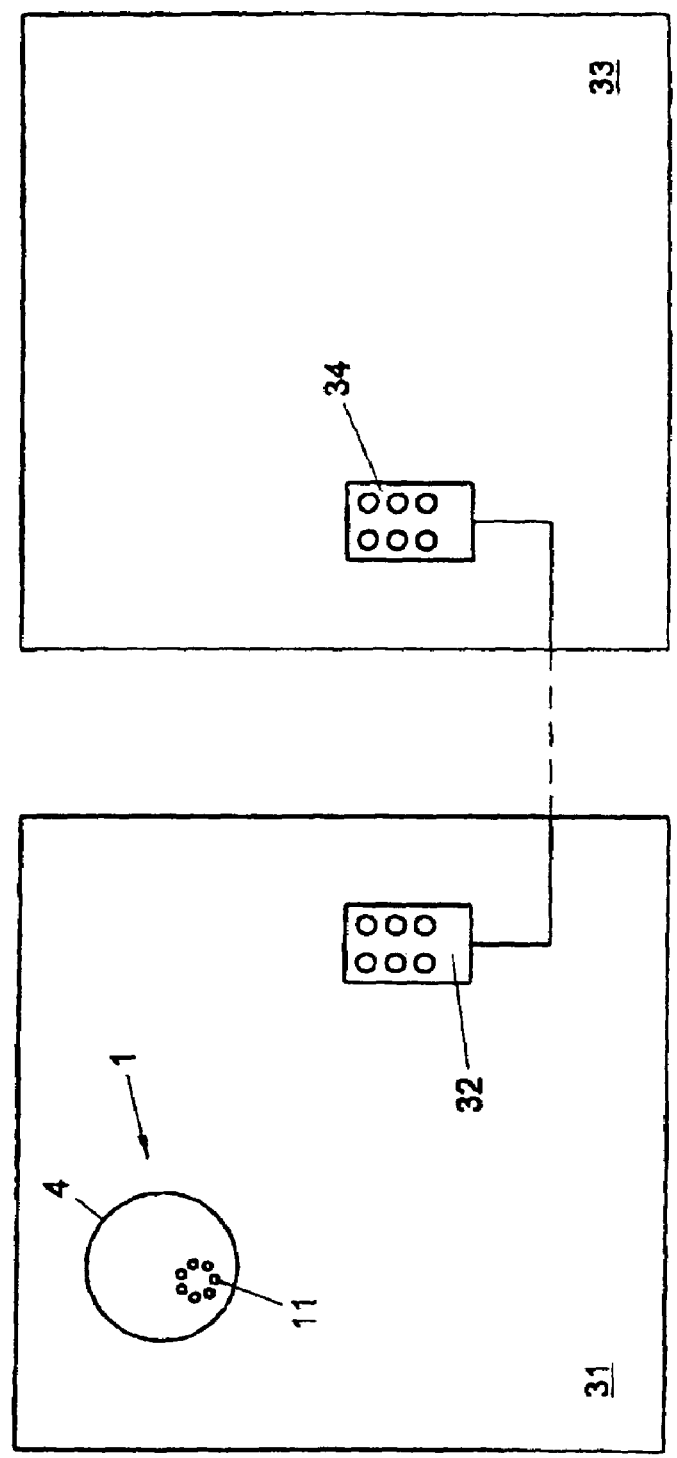
FIG. 4 schematically shows an alternative embodiment of an apparatus according to the invention.

FIG. 4 shows an alternative embodiment of an apparatus according to the invention, in which the sensor part 1 at least comprises acoustic means 11, for instance a generator for bleeps or a continuous signal. During use, the sensor part 1 is arranged in a first space 31, for instance on a child. Arranged in the same space 31, at any rate adjacent thereto, is a first baby alarm 32 of a baby alarm set, such that it can receive a signal generated by the acoustic means 11 of the sensor part 1, and pass it on to a second baby alarm of the same baby alarm set, arranged in a second space 33. In the embodiment shown, use has been made of a baby alarm set operating off an electricity grid. Of course, use can also be made of transmitting and receiving baby alarm sets which, for instance, operate on radiofrequency, while a baby alarm set may also comprise more than two baby alarms. A baby alarm set should herein be understood to be a set of at least two elements, of which a first element is arranged for at least picking up acoustic signals and transmitting them to at least the second element, which is arranged for at least reproducing the signals in question, for instance acoustically or visually. Also understood to be encompassed are sets of elements capable of communicating in two directions.

A sensor unit 8 according to the invention can contain different sensors known per se for registering movements. A number of these will be non-limitatively enumerated and described.

Figure 5:
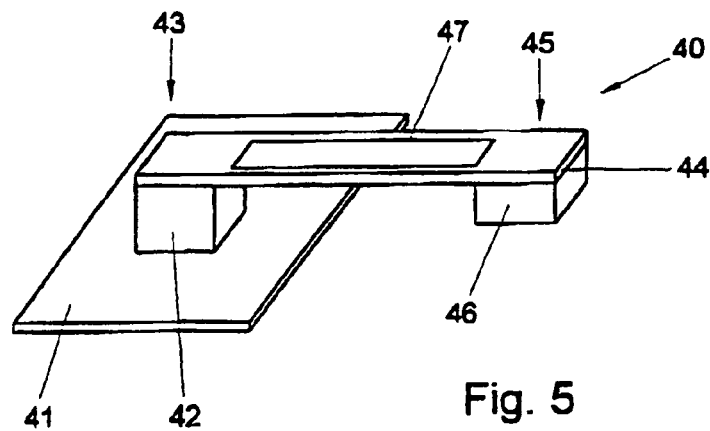
FIG. 5 schematically shows in perspective view a sensor for use in an apparatus according to the invention in a first embodiment.

FIG. 5 shows a first embodiment of a sensor 40, which comprises a base plate 41, for instance a portion of the housing 4 of a sensor part 1, on which base plate 41 a carrier 42 is arranged, on which, on the side remote from the base plate, a first end 43 of a strip-shaped carrier 44 is fixedly mounted. The second end 45 of the carrier 44 can move freely and has been weighted with a weight 46. Provided on the carrier 44, between the first end 43 and the second end 45, is at least one strain gauge strip 47, with which displacements of the second end 45 relative to the first end 43 can be measured, as well as movements and accelerations. Such a movement sensor 40 is simple in construction, sensitive to movements, robust, and can be made of relatively small design. A number of such sensors can be combined for registering movements and accelerations in different directions. Also, several strain gauges 47 can be provided on the carrier, for instance with sensitivity directions that cross each other, so that a single sensor 40 already enables determining different directions of movement.

Figure 6:
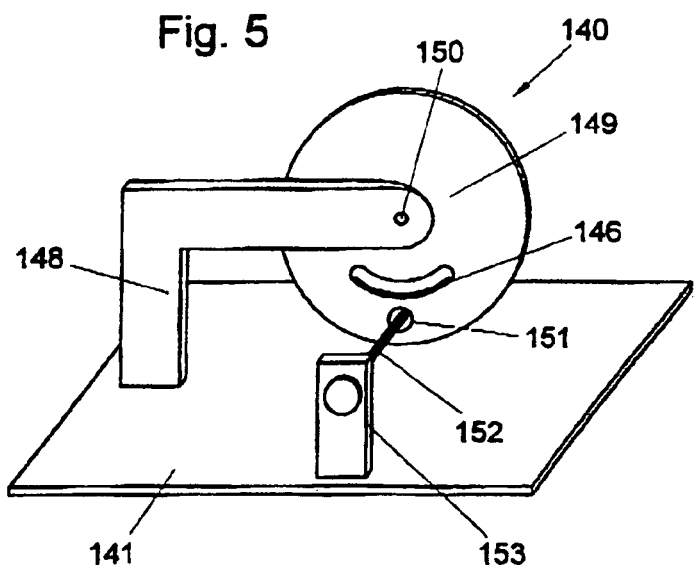
FIG. 6 schematically shows in perspective view a sensor for use in an apparatus according to the invention in a second embodiment.

FIG. 6 shows a second embodiment of a sensor 140, again comprising a base plate 141 which, via a bent arm 148, carries a rotatable disc 149. The disc 149 extends, for instance, in a plane at right angles to the base plate 141 and is rotatably suspended from the arm 148 in its center 150. On one side of the center 150, the disc 149 is weighted by a weight 146, such that when the plane of the disc 149 includes an angle with the horizontal, the weight will cause the disc 149 to rotate, such that the weight ends up centrally under the center 150. This is a preferred position of the disc 149. Below the weight 146, an opening 151 is provided in the disc 149, through which a light ray 152 of an optocoupler 153 can pass when the disc 149 has been brought into the preferred position mentioned. With the aid of the optocoupler, therefore, the preferred position of the disc 149 can be detected. If the movement sensor is moved, the disc 149 will rotate, which will be detected by the optocoupler since the light ray 152 is at least periodically interrupted by the disc 149.

It will be clear that instead of the opening, a reflective element can be used, while reflected light is detected by a suitable sensor. It is also possible to provide different openings or reflectors along the circumference of the disc 149, so that different positions of the disc 149 can be separately detected to enable even better determination of the movement pattern. These and similar variants will readily occur to those skilled in the art.

Figure 7:
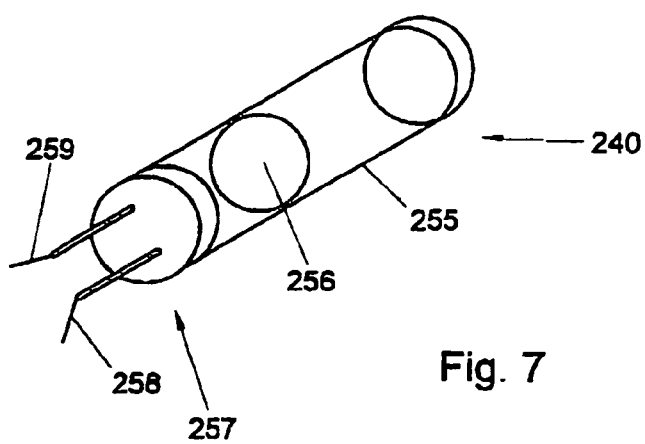
FIG. 7 schematically shows in perspective view a sensor for use in an apparatus according to the invention in a third embodiment.

FIG. 7 shows a third embodiment of a movement sensor 240 according to the invention, which, in the embodiment shown, consists of a tubular element 255, in which a ball-shaped element 256 is movably confined, such that this element 256 can move freely between the two ends of the tubular element 255. Arranged at one end 257 of the tubular element 255 are a number of electrically separated contacts 258, 259, which communicate with the central unit 6 of the sensor part 1. When the ball-shaped element 256 engages the two contacts 258, 259, these are conductively connected, so that an electrical circuit is closed and the intended position of the ball-shaped element is defined. Upon movement of the sensor part 1, the ball-shaped element 256 will move in the tubular element 255, thereby alternately enabling and non-enabling electrical conduction between the contacts 258 and 259. Consequently, movements and accelerations can be simply detected.

In the case of a sensor as shown in FIG. 7, naturally different embodiments can be utilized, for instance provided with a plurality of contacts 258, 259 adjacent one end, or contacts adjacent each of the ends of the tubular element. Further, contacts may additionally be incorporated in the sidewall of the tubular element. As a result, movements and accelerations can be detected even more accurately.

Further, other kinds of sensors can be utilized, such as, for instance, sensors of the unidirectional or omnidirectional switch type. Such a sensor comprises, for instance, an electrically conductive sphere, for instance solid or of mercury, received in a closed housing, which sphere, depending on the position of the switch, can make contact with two or more contacts included in the housing. Thus, positions and movements such as accelerations can be simply indicated. The housing may allow movements of the sphere in one or more directions. It is noted that the housing may then also function as one of the contacts.

Furthermore, traditional mercury switches or the like can be used, while the mercury, of course, may be replaced with a different suitable material.

It will be clear that also of the sensors 140, 240 shown in FIGS. 6 and 7, different ones can be combined for detecting movements in several directions, while all kinds of variant embodiments of these are possible.

For the processing of the signals in one of the central control units 6, 21, preferably use is made of an algorithm that is based on fuzzy logic, preferably of the self-learning type. Preferably, the various components of the sensor part as well as of the receiver are integrated into a microprocessor, yielding a relatively simple, robust and advantageous embodiment. Of course, discrete electronic components can be used as well.

Of course, it is also possible to build up algorithms differently, for instance as purely logic software.

The information transfer to the care giver can be provided for directly from the sensor part 1, for instance by audio or visual signals, but the information is preferably transferred from the receiver, or, for instance, a telephone apparatus 30. The user can set threshold values, while subsequently, when these are exceeded, for instance an alarm signal is produced. As described above, the threshold value can be selected, for instance, on the basis of the individual to be taken care of, age and the like. Further, threshold values or like presettings can be selected on the basis of the positions to be detected, for instance the belly position, supine position, side position, motional activity, and the like. The signals to be produced can be alarm signals as well as information signals of a different kind, for instance signals whose brightness, frequency or the like is made dependent on the extent of motional activity or the extent of change. These and many other variations are considered to be readily clear to those skilled in the art.

If the sensor part 1 is equipped with a microphone, as described earlier, the sensor part can also be attached near the individual, for instance a child, to a bed or crib or the like, while the apparatus can then function as baby alarm or intercom. Here, no use is made, at least not necessarily so, of the movement sensor present. The receiver may further comprise means for sending a check signal to the sensor part to verify whether the sensor part 1 is switched on and whether it is capable of communication, while the clip may, for instance, be so designed that when it is not clamped onto an article of clothing, a part of the clip and a part of the housing make contact and close a circuit, so that an alert signal is generated, indicating that the sensor part 1 has become detached and so does not function in the desired manner anymore. This increases safety still further.

The invention is not in any way limited to the exemplary embodiments represented in the description and drawings. Many variations thereof are possible.

Thus, a plurality of sensor parts 1 can be used with a receiver 20, while the different sensor parts 1 can have different communication frequencies, for distinction purposes. Further, instead of radio signals, light signals, audio signals and the like can be utilized for communication between a sensor part 1 and a receiver 20. Furthermore, between the sensor part 1 and the receiver 20, intermediate means may be arranged, for instance on the rim of a crib or bed, for amplifying and retransmitting relatively weak signals generated by the sensor part 1, which may be advantageous, for instance, when the sensor part 1 is wholly or partly screened off by the individual or by artifacts. Furthermore, a sensor part 1 according to the invention can naturally have all kinds of embodiments, while all kinds of fasteners can be used, for instance Velcro, clamping means, insertion means, adhesives and like fastening techniques known per se. Also, as energy supply for the sensor part, other means may be provided, and the apparatus may also be utilized for ambulant persons.

These and many comparable variations are understood to fall within the scope of the invention.

What is claimed is:

1. A method for registering movement patterns of lying positions of relatively young children, which comprises:
    attaching a sensor part to or onto a body part of an individual, said sensor part including at least one movement sensor and transmitting means for wireless transfer of a signal between said at least one movement sensor and a receiver;
    recording said signal to create a movement history of the individual; and
    generating an information signal.

2. A method according to claim 1, wherein in the movement history at least one time-related representation of the position of at least one part of a body of the individual in question is recorded, while a threshold time is set during which at least one specific position of the at least one part of the body is allowed, such that when this threshold time is exceeded, and depending on the movement history, an alarm signal is generated.

3. A method according to claim 2, wherein the at least one specific position, or a number of specific positions, is or are set prior to use of the sensor part.

4. A method according to claim 1, wherein prior to use of the sensor part, at least one allowable and/or at least one unallowable movement pattern is set, while the movement history is compared with the at least one movement pattern, on the basis of which comparison an alarm signal is generated or not.

5. An apparatus for registering a movement pattern of at least one part of a body of an individual, on a basis of a number of parameters, and generating a signal on the basis of at least one pre-set threshold value of at least one parameter or a set movement pattern for use in registering lying positions of relatively young children, which apparatus comprises:
    at least one sensor part including means for attachment to or onto a body part of an individual, and at least one movement sensor for registering movements of said body part
    a receiver, in particular a base station; and
    transmitting means and receiving means for wireless communication between the sensor part and the receiver, wherein said receiver records said signal to create a movement history of the individual.

6. An apparatus according to claim 5, wherein the at least one receiver is a first baby alarm or a baby alarm set, the at least one signal being at least acoustic.

7. An apparatus according to claim 6, wherein an algorithm is provided for comparing the registered movement pattern with a pre-set allowable and/or unallowable movement pattern and activating at least the alarm signal on the basis of this comparison.

8. An apparatus according to claim 5, wherein memory means are provided for storing at least a part of the registered movement history of the individual in question.

9. An apparatus according to claim 5, wherein means are provided for continuously or semicontinuously generating a signal via a base station, in which signal at least the instantaneous movement situation, an instantaneous posture and/or a part of the movement history are, at least is, encoded.

10. An apparatus according to claim 5, wherein setting means are provided for setting at least the at least one threshold value, allowable and/or unallowable movement patterns and kinds of signals.

11. An apparatus according to claim 5, wherein the sensor part comprises clamping means and a relatively smooth and flat, rounded housing.

12. An apparatus according to claim 5, wherein the sensor part comprises means for picking up audio signals, originating from breathing, and or heartbeat.

13. An apparatus according to claim 5, wherein means are provided for picking up via a telephone connection signals originating from the at least one movement sensor and/or any further registration means, while the sensor part comprises means for responding to a specific telephone signal, in particular a groupe speciale mobile connection.

* * * * *